United States Patent
Bell et al.

(10) Patent No.: US 6,187,425 B1
(45) Date of Patent: *Feb. 13, 2001

(54) ELASTIC MATERIALS WITH IMPROVED PERFORMANCE AT BODY TEMPERATURE

(75) Inventors: Anita S. Bell, Alpharetta; Lavada C. Boggs, Marietta; James R. Fitts, Jr., Gainesville; Audrie T. Ono, Atlanta; Oomman P. Thomas, Alpharetta, all of GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/855,108

(22) Filed: May 13, 1997

Related U.S. Application Data

(63) Continuation-in-part of application No. 08/777,503, filed on Dec. 30, 1996, now abandoned.

(51) Int. Cl.[7] .............................. C08L 53/00; A61L 15/22
(52) U.S. Cl. ...................... 428/221; 428/221; 428/910; 428/119; 525/89; 525/95; 525/98
(58) Field of Search ................................. 428/34.6, 34.7, 428/119, 221, 910; 525/89, 95, 98

(56) References Cited

U.S. PATENT DOCUMENTS

| | | |
|---|---|---|
| 3,383,435 | 5/1968 | Cizek . |
| 3,994,856 | 11/1976 | Katchman et al. . |
| 4,167,507 | 9/1979 | Haaf . |
| 4,259,220 | 3/1981 | Bunnelle et al. ............... 260/27 BB |
| 4,313,864 | 2/1982 | Haaf et al. . |
| 4,383,082 | 5/1983 | Lee, Jr. . |
| 4,414,970 | 11/1983 | Berry ................... 128/156 |
| 4,418,123 | 11/1983 | Bunnelle et al. ................... 428/517 |
| 4,421,883 | 12/1983 | Cooper et al. . |
| 4,423,187 | 12/1983 | Brandstetter et al. . |
| 4,525,407 | 6/1985 | Ness ....................... 428/138 |
| 4,525,508 | 6/1985 | Lee, Jr. . |
| 4,543,099 | 9/1985 | Bunnelle et al. ................ 604/385 A |
| 4,544,703 | 10/1985 | Haaf . |
| 4,719,261 | 1/1988 | Bunnelle et al. ....................... 525/97 |
| 4,728,461 | 3/1988 | Fujii et al. . |
| 4,816,345 | 3/1989 | Jadamus et al. . |
| 4,866,129 | 9/1989 | Brandstetter et al. . |
| 4,910,064 | 3/1990 | Sabee .................................... 428/113 |
| 4,957,799 | 9/1990 | Miyamoto et al. .................. 428/114 |
| 4,977,011 | 12/1990 | Smith .................................. 428/152 |
| 5,059,645 | 10/1991 | Ostermayer et al. . |
| 5,093,422 | 3/1992 | Himes ..................................... 525/98 |
| 5,100,959 | 3/1992 | Okada et al. . |
| 5,109,068 | 4/1992 | Yamasaki et al. . |

(List continued on next page.)

FOREIGN PATENT DOCUMENTS 0 606 931 A2   7/1994   (EP) .

OTHER PUBLICATIONS

Kirk–Othmer, The Encyclopedia of Chemical Technology, vol. 19, pp. 678–691.
Database WPI Week 8841, Derwent Publications Ltd., London, GB; AN 88–246781 XP0020647890, for JP 63 179 956 a (Asahi Chem Ind Co Ltd) Jul. 23, 1988.
Database WPI Week 8126, Derwent Publications Ltd., London, GB: AN 81–46620D, XP002064791 for JP 56 051 356 A (Asahi Dow Ltd), May 8, 1981.

*Primary Examiner*—Richard Weisberger

(57) ABSTRACT

Laminate compositions with significantly improved retention of elastic and mechanical properties such as stress relaxation, permanent set, elongation modulus and hysteresis and modulus at temperatures slightly above body temperature, under actual use conditions, are formed from polymeric materials containing styrene copolymers and polymeric compounds blended with polyphenylene ether.

13 Claims, 4 Drawing Sheets

U.S. PATENT DOCUMENTS

| | | |
|---|---|---|
| 5,109,069 | 4/1992 | Shibata et al. . |
| 5,118,748 | 6/1992 | Fujita et al. . |
| 5,124,415 | 6/1992 | Sakamoto et al. . |
| 5,166,264 | 11/1992 | Lee, Jr. et al. . |
| 5,189,099 | 2/1993 | Arnold-Mauer et al. . |
| 5,209,801 | 5/1993 | Smith .................................. 156/161 |
| 5,288,791 | 2/1994 | Collier, IV et al. . |
| 5,296,540 | 3/1994 | Akiyama et al. . |
| 5,304,599 | 4/1994 | Himes .................................. 525/98 |
| 5,324,782 | 6/1994 | Lee, Jr. . |
| 5,397,822 | 3/1995 | Lee, Jr. . |
| 5,418,275 | 5/1995 | Okada et al. . |
| 5,503,908 | 4/1996 | Faass .................................. 428/198 |
| 5,652,041 | 7/1997 | Buerger et al. .................... 428/198 |
| 5,705,556 | 1/1998 | Djiauw et al. ..................... 524/505 |

ELASTIC MATERIALS WITH IMPROVED PERFORMANCE AT BODY TEMPERATURE

This application is a continuation-in-part of Ser. No. 08/777,503 filed Dec. 30, 1996, now abandoned.

FIELD OF INVENTION

The present invention pertains to polymeric materials with improved elastic performance at body temperature and laminates thereof. The polymeric materials of the present invention are particularly useful in disposable personal care products in which good body conformance and retention of product shape over time, at body temperature, are required.

BACKGROUND OF THE INVENTION

Polymeric materials have a wide variety of uses, especially in the areas of absorbent articles and disposable items. As used herein, the term "absorbent articles" refers to devices which absorb and contain body exudates and, more specifically, refers to devices that are placed against or in proximity to the body of the wearer to absorb and contain the various exudates discharged from the body. The term "absorbent articles" is intended to include diapers, training pants, absorbent underpants, incontinence products, bandages and the like. The term "disposable" is used herein to describe articles not intended to be laundered or otherwise restored or reused, such as protective articles including industrial work wear and medical garments such as surgical drapes and gowns, as well as other articles of clothing either as the entire article or simply as a component thereof.

Thermally and solution-processed elastomers are commonly used in disposable personal care absorbent articles for waist bands, side panels and other gasketing applications. In the case of waist bands and side panels, the elastomer functions to hold the article in place during and under actual use conditions. Actual use conditions typically involve heat, humidity, loading or any combination thereof. In the case of gaskets, the elastomer functions to hold the disposable personal care absorbent article closer to the wearer's skin and thereby prevent leakage. The gaskets also manage some stress and prevent sagging of the absorbent article over a certain period of time. Some of these elastomers, however, lose their elastic properties after a period of exposure to actual use conditions.

Lycra strand is an excellent elastomer and performs well at body temperature. The superior elastic properties result from the well-defined, phase-segregated molecular structure of Lycra strand. In general, Lycra strand is a two-phase polymer system having a hard phase and a soft phase. The phase segregation occurs between the hard and soft rubber segments which constitute the backbone of the polymer. Lycra strand behaves almost like an ideal elastomer because of the substantial difference in the glass transition, or melting point, of the rubber block and the glass transition of the urea, hard segment. Lycra strand, however, is expensive because (1) it is produced by wet spinning and (2) there is a lack of competitive products on the market.

There are other block copolymers based on urethane or ester that attempt to take advantage of the concept of phase segregation. These copolymers include polyurethane elastomeric materials such as, for example, those available under the trademark ESTANE® from B. F. Goodrich & Company of Akron, Ohio and those available under the trademark MORTHANE® from Morton International, Inc. of Seabrook, New Hampshire and polyester elastomeric materials such as, for example, those available under the trade designation HYTREL® from E. I. Dupont de Nemours & Company of Wilmington, Del. and those known as ARNITEL®, formerly available from Akzo Plastics of Arnhem, Holland and now available from DSM of Sittard, Holland. Such urethane and ester copolymers, while capable of delivering excellent elastic properties, can be costly. They are, therefore, not always cost effective for use in the business of disposable personal care absorbent articles.

Thermoplastic block copolymer elastomers based on blocks of polystyrene and rubber blocks of isoprene, butadiene, siloxane, amorphous ethylene, propylene or a combination of amorphous ethylene and propylene, are attractive for use in disposable personal care absorbent articles because of the lower cost, the ease of processing and the non-toxicity. However, at body temperature, these copolymers lose their elastic properties and dimensional stability after a period of time and begin to sag and leak. The loss of elastic properties and dimensional stability appears to be associated with the polymer itself. The segments of polystyrene begin to flow and slip at the normal human body temperature, especially under tension or load. The motion of the styrene blocks adversely affects the elastic character of the polymer, resulting in the loss of dimensional stability and elastic properties.

A need, therefore, exists for a cost-effective polymer that retains its elastic properties while also having increased mechanical properties and that is useful personal care absorbent articles such as diapers, training pants, incontinence devices and the like.

Similarly, in protective articles such as industrial work wear and medical garments, the motion of the styrene blocks adversely affects the elastic character of the polymer, resulting in the loss of dimensional stability and shape. A need, therefore, exists for a polymer that imparts improved in-use durability to such protective articles.

SUMMARY OF THE INVENTION

It has now been discovered that preventing the flow of styrene blocks results in a polymeric material with significantly improved retention of elastic properties and improved performance at body temperature. Thus, in accordance with the present invention, polymeric material is derived from styrene block copolymers blended with polyphenylene ether. Polyphenylene ether is a high performance thermoplastic having relatively high melt viscosities, a high glass transition temperature (typically, $T_g$=210° C., but $T_g$ may vary as a function of molecular weight) and a high softening temperature ($T_g \geq 275$° C.).

As used herein, the term "dimensionally stable" means resistant to creep or able to retain its shape as a function of time under actual use conditions.

As used herein, the term "body temperature" means about 98.6° F. ±4° F.

Polymeric materials produced according to the present invention may be used as elastic components of personal care absorbent articles such as, for example, in the side panels of diapers and training pants, as well as in the leg elastic and gasketing of diapers, training pants, incontinence devices and the like. They may also be used in protective garments such as industrial work wear and surgical drapes and gowns.

The foregoing and other features and advantages of the present invention will become apparent from the following detailed description of the presently preferred embodiments, when read in conjunction with the accompanying examples.

DETAILED DESCRIPTION OF THE PREFERRED EMBODIMENTS

Figure 1:
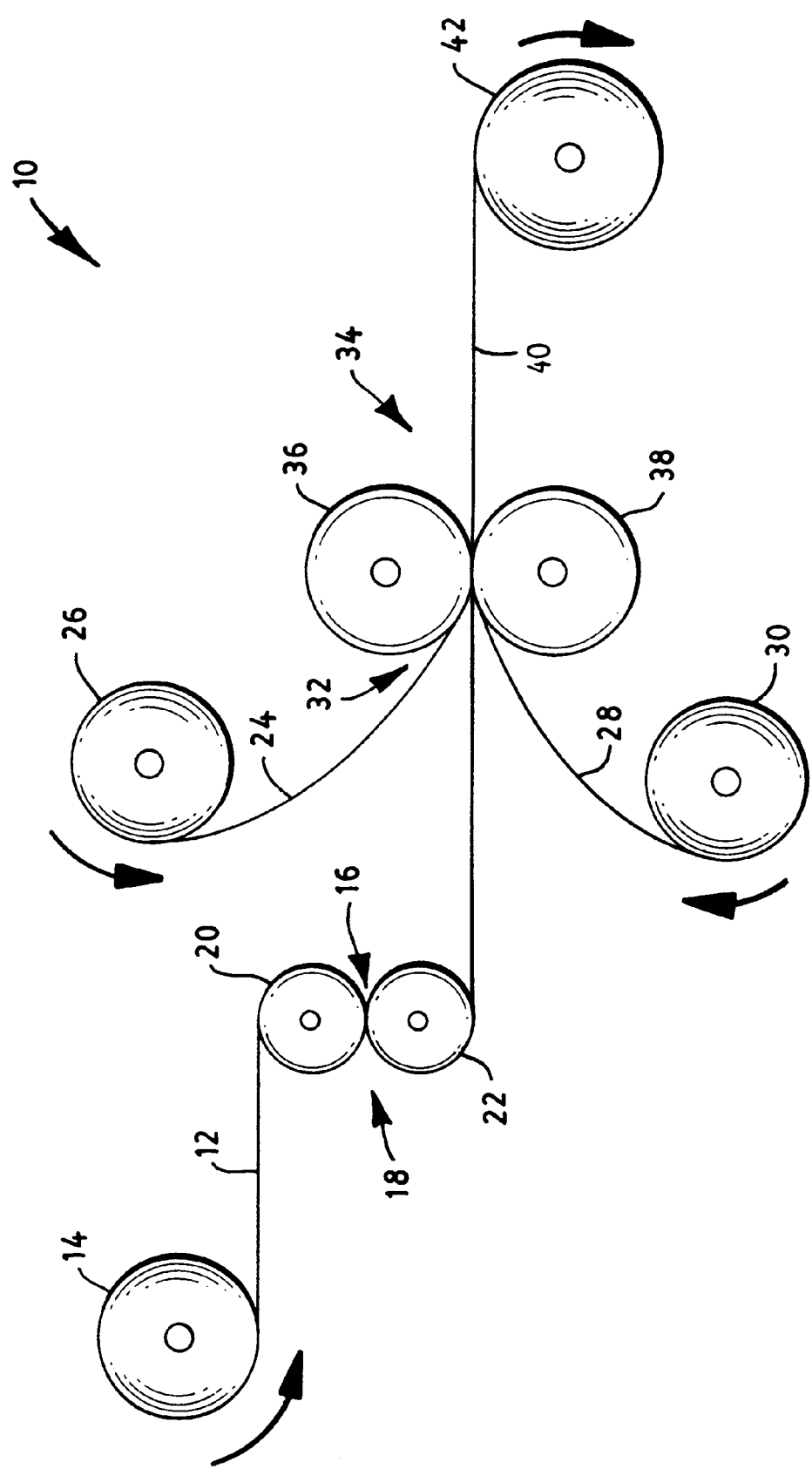
FIG. 1 is a schematic diagram of a process for forming an elastic laminate of the present invention.

The present invention is directed to a low cost, highly elastic polymeric material that retains its shape and key elastic properties at slightly to moderately elevated temperatures above the normal human body temperature. The polymeric material of the present invention is formed using a blend of a styrene-based elastic material and polyphenylene ether (PPE).

Materials that are useful in the present invention are generally known as "elastomers." An elastomer is a rubber elastic material capable of stretching to several times its original, relaxed length and which tends to recover completely its elongation upon release of the stretching, biasing force. As used herein, the term "recover" refers to a contraction of a stretched material upon termination of a biasing force following the stretching of the material by application of the biasing force. Examples of these materials are indexed as "elastomers" in Bradley et al., *Materials Handbook*, 284–290 (McGraw-Hill, Inc. 1991), which is incorporated herein by reference. The physical structure of the elastomer can be in the form of strands, cast or blown film or any non-woven web of fiber of a desired thermoplastic polymer.

Useful elastomers include block copolymers having the general formula A-B-A' where A and A' are each rigid glassy blocks of polystyrene separated by a rubber block, B. The rubber block may be, for example, polybutadiene, polyisoprene, polyethylene, polypropylene and combinations of polyethylene and polypropylene. The rubber blocks typically have very low glass transition temperatures, i.e., well below room temperature. The rigid glassy blocks generally have glass transition temperatures above room temperature.

Preferred commercial examples of such elastomeric copolymers are those available under the trademark KRATON® from Shell Chemical Company of Houston, Tex. KRATON® block copolymers are available in several different formulations, a number of which are identified in U.S. Pat. Nos. 4,663,220; 4,323,534; 4,834,738; 5,093,422; and 5,304,599 which are incorporated herein by reference. Examples include KRATON® G polymers and compounds thereof.

Polymers composed of an elastomeric A-B-A-B tetrablock copolymer may also be used in the practice of this invention. Such copolymers are discussed in U.S. Pat. No. 5,332,613 to Taylor et al. which is incorporated herein by reference. In such polymers, A is a styrene block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene), or SEPSEP, elastomeric block copolymer which is commercially available from the Shell Chemical Company of Houston, Tex. under the trade name KRATON® G 6912.

The polymer/polyphenylene ether blends of the present invention have about a 1:1 ratio of styrene to polyphenylene ether. Thus, if the blend contains x% of styrene, then the weight percentage of polyphenylene ether is also x%.

The polymeric materials of the present invention may be formed using any one of the conventional processes known to those familiar with film formation. In general, the styrene block copolymer is blended with the appropriate amount of polyphenylene ether. The mixture is then heated and extruded into a monolayer or multilayer film using any one of a variety of film producing processes such as, for example, cast and embossed, chill and flat cast, co-extrusion and blown film processes.

Oftentimes it is desirable to laminate elastic films, strands or nonwovens to enhance the functions, strength and durability of the films, strands and nonwovens. Lamination of such materials is described in U.S. Pat. No. 5,385,775 to Wright and Ser. No. 08/777,505, filed Dec. 30, 1996 and its continuation, Case No. 659/277, filed May 13, 1997, all of which are incorporated herein by reference.

Referring to FIG. 1, there is schematically illustrated at 10 a process for forming an elastic laminate according to the present invention. Generally the film, strand or nonwoven 12 is unwound from a supply roll 14 and travels in the direction indicated by the arrow associated therewith as the supply roll 14 rotates in the direction of the arrows associated therewith. The film, strand or nonwoven 12 passes through a nip 16 of the S-roll arrangement 18 formed by the stack rollers 20 and 22.

A first gatherable layer 24 is unwound from a supply roll 26 and travels in the direction of the arrow associated therewith as the supply roll 26 rotates in the direction of the arrows associated therewith. A second gatherable layer 28 is unwound from a supply roll 30 and travels in the direction of the arrow associated therewith as the supply roll 30 rotates in the direction of the arrows associated therewith.

The first gatherable layer 24 and the second gatherable layer 28 pass through the nip 32 of the bonder roll arrangement 34 formed by the bonder rollers 36 and 38. The first gatherable layer 24 and/or the second gatherable layer 28 may be formed by extrusion processes such as, for example, meltblowing, spunbonding or film extrusion processes and passed directly through the nip 32 without first being stored on a supply roll.

The film, strand or nonwoven 12 passes through the nip 16 of the S-roll arrangement 18 in a reverse S-path as indicated by the rotation direction arrows associated with the stack rollers 20 and 22. From the S-roll arrangement 18, the film, strand or nonwoven 12 passes through the pressure nip 32 formed by a bonder roller arrangement 34. Because the peripheral linear speed of the rollers of the S-roll arrangement 18 is controlled to be less than the peripheral linear speed of the rollers of the bonder roller arrangement 34, the film, strand or nonwoven 12 is tensioned between the S-roll arrangement 18 and the pressure nip of the bonder roll arrangement 34. By adjusting the difference in the speeds of the rollers, the film, strand or nonwoven 12 is tensioned so that it stretches a desired amount and is maintained in such stretched condition while the first gatherable layer 24 and the second gatherable layer 28 are joined to the film, strand or nonwoven 12 during their passage through the bonder roll arrangement 34 to form an elastic laminate 40. The elastic laminate 40 immediately relaxes upon release of the tensioning force provided by the S-roll arrangement 18 and the bonder roll arrangement 34, whereby the first gatherable layer 24 and the second gatherable layer 28 are gathered into the elastic laminate 40. The elastic laminate 40 is then wound up on a winder 42.

The advantages and other characteristics of the present invention are best illustrated by the following examples. It should be understood that the following examples are illustrative and are not limiting.

EXAMPLES

Control elastic materials made from pure polymers and inventive elastic materials made from styrene block copolymers modified with polyphenylene ether were tested for stress relaxation, mechanical properties and hysteresis according to the following procedures:

STRESS RELAXATION

Stress relaxation is defined as the force required to hold a given elongation constant over a period of time. For the actual test, film samples of about 3 inches wide and 4–5 millimeters thick were tested in a Sintech 1/ S testing frame in an environmental chamber at about 100° F. The initial 3-inch grip to grip distance of the sample was displaced to 4.5 inches (50% elongation) at a cross-head displacement speed of 20 inches per minute. The stress relaxation (or load loss) as a function of time was measured over a period of 12 hours. The rate of the change of the load (modulus) as a function of time was obtained by calculating the slope of a log-log regression of the stress relaxation modulus and time. A perfect elastic material such as, for example, a metal spring will give a zero slope and a zero load loss.

MECHANICAL PROPERTIES

The stress elongation behavior of the samples made using the blends of the present invention were obtained at room and body temperature using an Instron 1200 and a Sintech 1/ S testing frame. Film samples in the shape of a dog bone were approximately 0.03 inches thick and 0.5 inches wide. The grip to grip distance was 2 inches. The cross-head displacement speed was 2 inches per minute. The load was normalized with respect to the cross-sectional area to obtain the stress. The elongation was calculated from a knowledge of the original length and of the change in length of the samples.

HYSTERESIS

Equilibrium hysteresis behavior of the polymers was obtained by ramping a rectangular specimen up to 50% elongation and down to 0% elongation at 20 inches per minute at room temperature. This procedure was repeated 10 times. Most of the samples attained equilibrium in 2 to 3 repetitions. The data was acquired at a rate of 100 samples per second to give a well-defined loop. Data collected was further smoothed using a smoothing routine. Hysteresis was calculated by the integration of the smoothed data using the Simpson rule. The Simpson rule is a method used for computing the approximate area bounded by a curve by adding the areas of a series of figures formed from an odd number of equally spaced ordinates to the curve and parabolas drawn through the points where these ordinates cut the curve. The difference in energy between the loading and unloading curves was divided by the initial loading energy and multiplied by 100 to obtain the percentage hysteresis.

The following polymers and polymeric compounds were used in the above-described testing procedures: KRATON® G 6906, a triblock copolymer of styrene-β-ethylenepropylene-β-styrene; KRATON® G 6912, a copolymer of styrene-β-ethylenepropylene-β-styrene-β-ethylenepropylene; KRATON® RP 6608, which is a polymeric compound of KRATON® G 6906, a tackifier and polyethylene wax; KRATON® RP 6588, a polymeric compound of KRATON® G 6912, a tackifier and polyethylene wax; KRATON® SEQ 1657, a sequentially coupled diblock-free copolymer of styrene-β-ethylenepropylene-β-styrene; and KRATON® 1659, a diblock styrene-β-ethylenepropylene-β-styrene copolymer.

The inventive blends of styrene block copolymers and polyphenylene ether all contained about a 1:1 ratio of styrene to polyphenylene ether. For example, KRATON® G 6912 contains about 21% styrene and 79% rubber. Hence, a blend of about a 1:1 ratio means there is about an equal percent of styrene from within the KRATON® G 6912 and polyphenylene ether.

Table I below shows the slope and the rate of actual load loss over a 12-hour period as determined from the stress relaxation experiment described earlier. The slope can be calculated using the following power law model to obtain the exponent m:

$$\text{Load}_{@time\ t} = (\text{Load}_{@t=0})\,(t^{-m})$$

wherein t is time and m represents how fast the material loses its load. Table I also shows the actual load loss after 12 hours for all the control and inventive elastic materials tested. Elastic material IDs 1–3 contain triblock copolymer, of styrene in the KRATON® G 6906. Control material 1 is made using pure KRATON® G 6906. Elastic material 2 consists of about a 1:1 blend of KRATON® G 6906 and polyphenylene ether made according to the present invention. The blend contains about 18% styrene (the amount found in the pure KRATON® polymer) and thus, about 18% polyphenylene ether. Elastic material 3 is made using an inventive blend of KRATON® RP 6608 (compounded KRATON® G 6906) and polyphenylene ether. As seen in Table I, the addition of polyphenylene ether to the base polymer decreases the magnitude of the slope and load loss favorably. The stress relaxation test on elastic material 2 shows about a 55% decrease in the slope and about a 36% decrease in the load loss as compared to control material 1. Thus, there is a significant improvement in stress relaxation when polyphenylene ether is added to the polymer in accordance with the present invention. The addition of tackifier and polyethylene wax in elastic material 3 indicates that stress relaxation is still improved over the pure polymer, but is not as good as the blend of the polymer with polyphenylene ether.

Elastic materials 5–7 were made from a pure polymer (KRATON® G 6912), a blend of KRATON® G 6912 and polyphenylene ether in a ratio of about 1:1 styrene (in the KRATON® polymer) and polyphenylene ether and a blend of KRATON® RP 6588 (compounded KRATON® G 6912) and polyphenylene ether in a ratio of about 1:1 styrene (in the KRATON® polymer) and polyphenylene ether, respectively. As was the case with elastic materials 1–3, the effect of the addition of polyphenylene ether to both the polymer and the polymeric compound is a lower slope and load loss. Again, the elastic material containing the compounded polymer (ID 7) showed improved stress relaxation over the control material (ID 5) but did not exhibit as much as an improvement as the elastic material containing the blend of the pure polymer and polyphenylene ether (ID 6).

Figure 2:
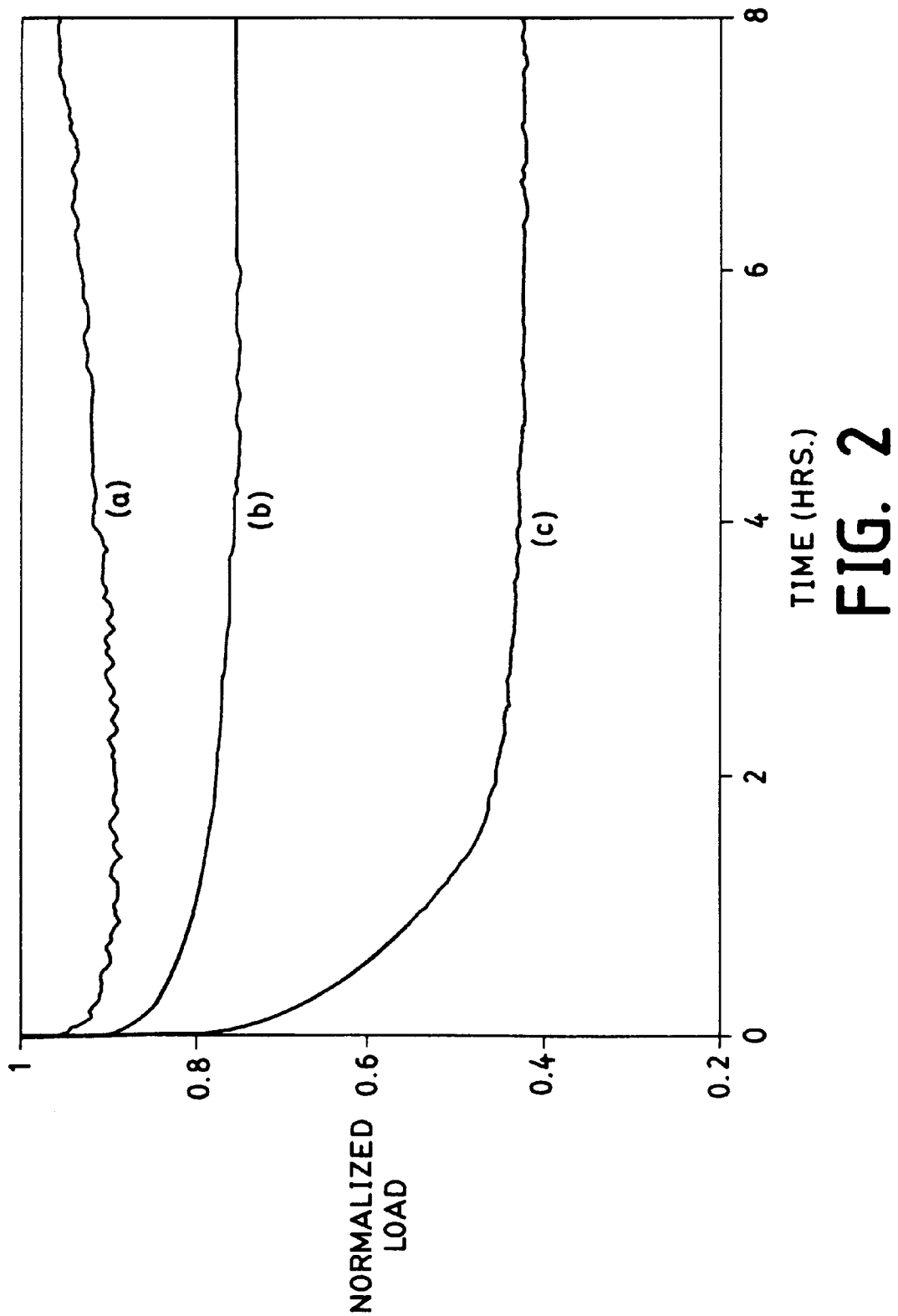
FIG. 2 is a graph of normalized load versus time in hours for (a) Lycra strand, (b) a film made according to the present invention and (c) a control film.

FIG. 2 is a graph of normalized load versus time for control elastic material 5 (curve c), elastic material 6 (curve b) and a material made from Lycra strand (curve a). The graph indicates that the load loss yields an exponential decay curve as a function of time. Lycra strand has a slope of –0.02 and a load loss 9%. The control has a slope of –0.11 and a load loss of 57%. Elastic material 6 has a slope of –0.03 and a load loss of 25%. As seen in FIG. 2, the addition of polyphenylene ether to the base polymer results in a substantial improvement in the stress relaxation (curve b).

Use of the diblock-free sequential 1657 in elastic material 11 gave surprising results. It can be seen from Table I that the magnitudes of the slope and the load loss for elastic material 11 are less than that of other pure KRATON® polymers, i.e., elastic materials 1 and 5. Addition of polyphenylene ether at about a 1:1 ratio further reduced the magnitudes of slope and the load loss in elastic material 12.

Addition of polyphenylene ether to styrene in the KRATON® 1659 in about a 1:1 ratio in elastic material 13 gave results similar to the other polymers previously discussed.

Generally, stress relaxation behavior in elastic materials containing a blend of styrene block copolymer and polyphenylene ether, as tested at body temperature for a 12-hour period, consistently yielded significant improvements over elastic materials not containing a blend of styrene block copolymer and polyphenylene ether. Additionally, the degree to which the stress relaxation performance improved was comparable regardless of whether the styrene block copolymer blended with polyphenylene ether was in its pure or compounded form.

TABLE I

Stress Relaxation Behavior at 100° F.

| ID | Description | Slope | Load Loss (%) |
| --- | --- | --- | --- |
| 1 | KRATON ® G 6906 | −0.11 | 56 |
| 2 | KRATON ® G 6906 + PPE | −0.05 | 36 |
| 3 | KRATON ® RP 6608 + PPE | −0.07 | 45 |
| 4 | KRATON ® RP 6608 | −0.12 | 58 |
| 5 | KRATON ® G 6912 | −0.11 | 57 |
| 6 | KRATON ® G 6912 + PPE | −0.05 | 36 |
| 7 | KRATON ® RP 6588 + PPE | −0.06 | 41 |
| 8 | KRATON ® RP 6588 + PPE | −0.05 | 43 |
| 9 | KRATON ® RP 6588 + PPE (1:0.75; 0.13 i.v.) | −0.06 | 39 |
| 10 | KRATON ® RP 6588 + PPE (1:0.5; 0.13 i.v.) | −0.06 | 40 |
| 11 | KRATON ® SEQ 1657 | −0.06 | 40 |
| 12 | KRATON ® SEQ 1657 + PPE | −0.05 | 35 |
| 13 | KRATON ® G 1659 + PPE | −0.05 | 37 |

Table I above also shows the effect of intrinsic viscosity (i.v.) of polyphenylene ether on the elastic and mechanical properties of the polymeric compound. Intrinsic viscosity is a measure of the molecular weight of a given polymer. In general, the higher the intrinsic viscosity, the higher the molecular weight. The molecular weight of polyphenylene ether must be comparable to that of the styrene block in the polymer in order to achieve maximum compatibility. When 0.3 i.v. polyphenylene ether is blended with styrene block copolymers, about a 1:1 ratio of styrene to polyphenylene ether is essential to obtain a thermally stable elastic material having a low slope and a low load loss. The results of elastic materials 8–10 in Table I indicate that the addition of 0.13 i.v. polyphenylene ether, irrespective of the ratio (i.e., 1:1, 1:0.75 or 1:0.5) yields excellent slope and load loss values. The slope and load loss values are almost identical regardless of the ratio of styrene block copolymer to polyphenylene ether. The lower i.v. polyphenylene ether is more cost efficient, however, because a lower concentration of polyphenylene ether can be used while still achieving substantially improved elastic properties. Thus, the lower i.v. polyphenylene ether Is preferred.

Figure 3:
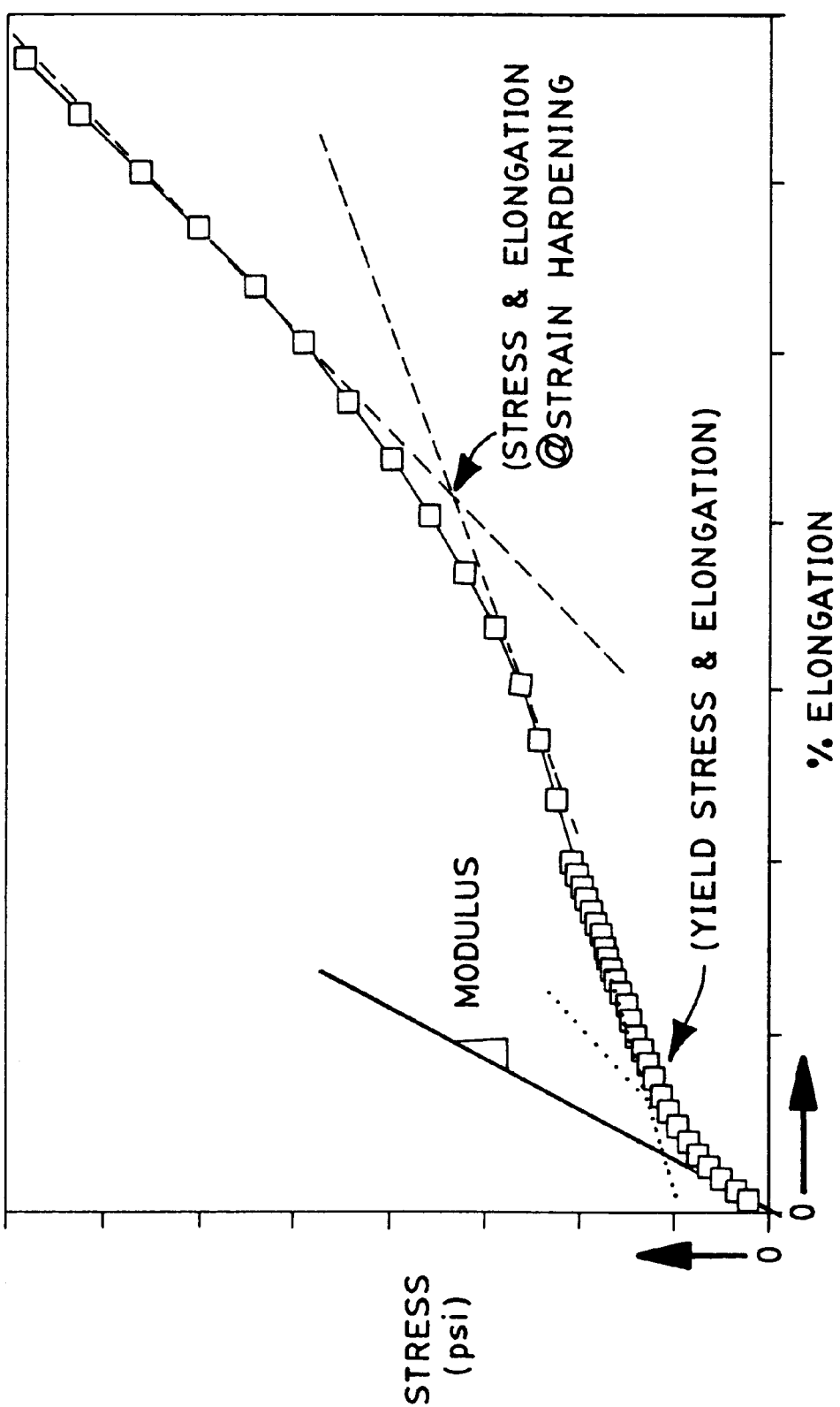
FIG. 3 is a graph of a typical stress-elongation curve defining various terms.

FIG. 3 shows a typical stress-elongation curve. FIG. 3 also schematically identifies the definitions of various parameters such as modulus, stress and percent elongation at yield and stress and percent elongation at strain hardening.

Table II shows the modulus, stress and percent elongation at yield and the stress and percent elongation at strain hardening for elastic materials made from the base copolymers and from the inventive blends of styrene block copolymers and polyphenylene ether. These mechanical parameters were obtained from a stress elongation test at body temperature. As can be seen from Table II, the addition of 0.3 i.v. polyphenylene ether to KRATON® G 6906 and KRATON® G 6912 increases the modulus and the stress at strain hardening. Addition of polyphenylene ether to the compounded versions (RP 6608 and RP 6588), however, results in mechanical properties much like those of the pure copolymers. In the case of KRATON® G 6912 blended with 0.3 i.v. polyphenylene ether, a broader variation in the modulus and stress at strain hardening occurs. This variation is most likely attributed to the batch to batch variation in the homogeneity of the blend. However, the addition of 0.13 i.v. polyphenylene ether to the compounded KRATON® G 6912 (RP 6588) seems to eliminate his variation.

TABLE II

Mechanical Properties of The Elastomers At 100° F.

| Sample ID | Modulus (psi) | Stress at Yield (psi) | Percent Elongation at Yield | Stress at Strain Hardening | Percent Elongation at Strain Hardening |
| --- | --- | --- | --- | --- | --- |
| RP 6608 | 388 | 115 | 30 | N/A | N/A |
| KG 6912 | 397 | 116 | 30 | 420 | 290 |
| RP 6588 | 404 | 119 | 30 | 420 | 291 |
| KG 1657 + PPE | 400 | 125 | 34 | 236 | 253 |
| KG 6906 + PPE (1:1) | 570 | 150 | 20 | 400 | 250 |
| KG 6912 + PPE (1:1) | 600 | 130 | 20 | 520 | 225 |
| RP 6588 + PPE (1:1) | 400 | 110 | 20 | 270 | 240 |
| RP 6588 + 0.13 PPE (1:1) | 410 | 110 | 22 | 230 | 260 |
| RP 6588 + 0.13 PPE (1:0.5) | 405 | 90 | 20 | N/A | N/A |
| RP 6588 + 0.13 PPE (1:0.75) | 420 | 100 | 20 | 240 | 270 |
| SEQ KG 1657 + PPE | 500 | 135 | 25 | 335 | 250 |

The equilibrium percentage hysteresis (%H) and permanent set (%S) for elastic materials made from the pure and compounded KRATON® polymers according to the present invention are shown in Table III. As can be seen from this table, blends of KRATON® G 6906 and 6912 polymers and 0.3 i.v. polyphenylene ether in ratios of about 1:1 and about 1:0.5 styrene in the KRATON® polymer to polyphenylene ether result in lower equilibrium hysteresis and permanent set for the resulting elastic materials. However, the addition of polyphenylene ether to a compounded polymer resulted in increased values. The increase was most likely caused by the plasticizing effect of the tackifier and polyethylene wax.

Table IV below shows the stress relaxation behavior at 100° F. of nonwoven-based laminates made using the elastic materials of the present invention as described above and in above-mentioned U.S. Pat. No. 5,385,775. Control laminate 1 is made using elastic materials comprising pure Kraton RP 6588, while inventive laminate 2 is made from elastic materials containing a 1:1 blend of styrene in the Kraton RP 6588 and 0.13 i.v. polyphenylene ether. Similarly, control laminate 3 is made from elastic materials containing pure Kraton RP 6608, and laminate 4 is made from elastic materials made from an inventive 1:1 blend of styrene in the Kraton RP 6608 and 0.13 i.v. polyphenylene ether. As seen in Table IV, the laminates made 5 using elastic materials according to the present invention have decreased slope and load loss at 100° F. Thus, there is a significant improvement in stress relaxation behavior of laminates made using elastic materials containing a blend of polymer and polyphenylene ether according to the present invention.

TABLE III

Hysteresis Properties for Elastic Materials at 100° F.

| Description | % Hysteresis | % Set |
|---|---|---|
| KRATON ® G 6906 | 4 | 6 |
| KRATON ® G 6906 + PPE (1:0.5) | 2 | 6 |
| KRATON ® G 6906 + PPE (1:1) | 2 | 3 |
| KRATON ® G 6912 | 9 | 13 |
| KRATON ® G 6912 + PPE (1:0.5) | 7 | 8 |
| KRATON ® G 6912 + PPE (1:1) | 7 | 7 |
| KRATON ® SEQ 1657 | 5 | 9 |
| KRATON ® SEQ 1657 + PPE (1:1) | 8 | 9 |

TABLE IV

Stress Relaxation Behavior of Laminates at 100° F.

| ID | Description | Slope | Load Loss (%) |
|---|---|---|---|
| 1 | RP 6588 | −0.1 | 55 |
| 2 | RP 6588 + PPE (1:1; 0.13 i.v.) | −0.05 | 27 |
| 3 | RP 6608 | −0.1 | 57 |
| 4 | RP 6608 + PPE (1:1; 0.13 i.v.) | −0.04 | 24 |

Figure 4:
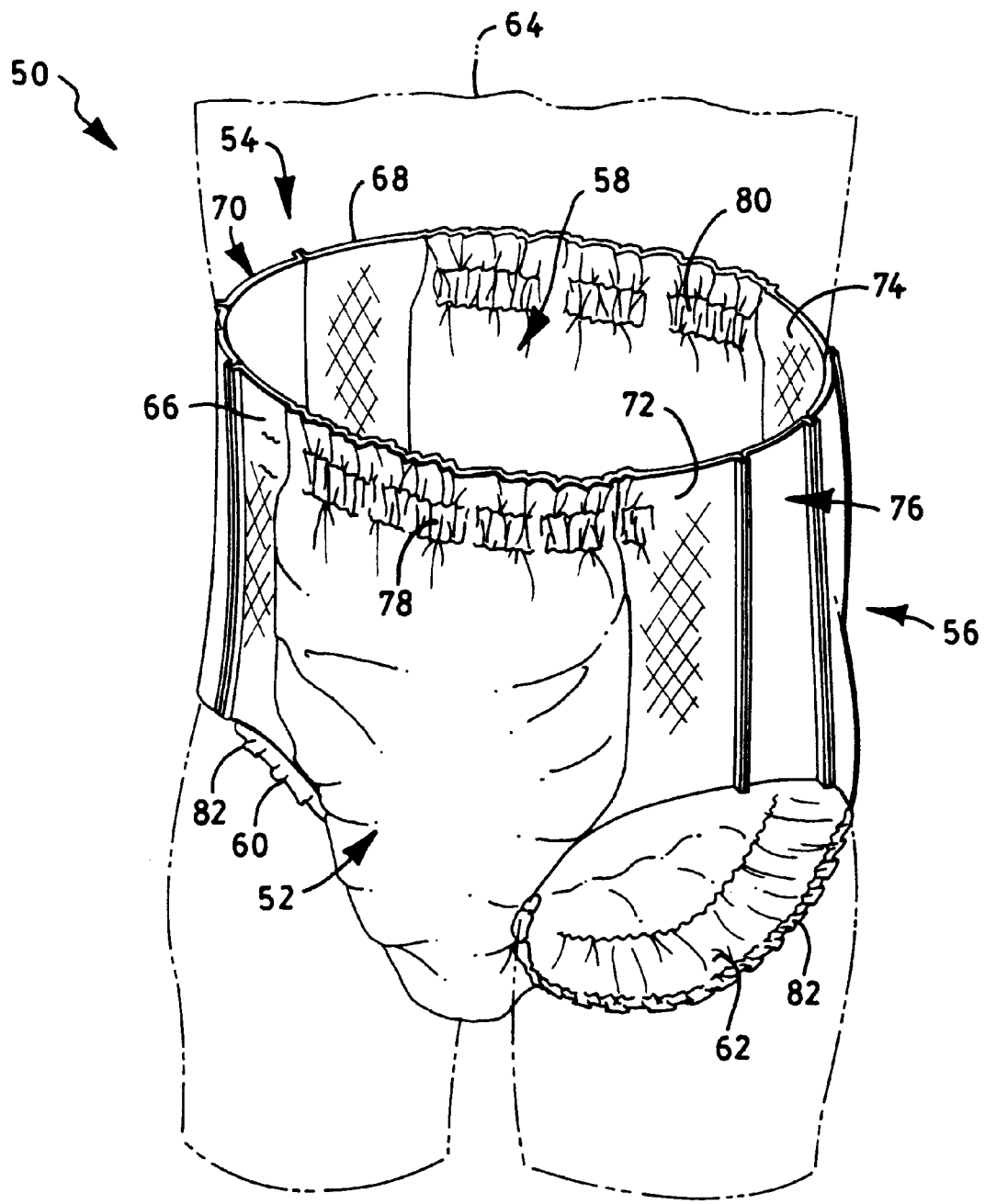
FIG. 4 is a perspective view of an exemplary disposable garment, in this case training pants, that utilizes the laminate material made according to the present invention.

Referring now to FIG. 4 of the drawings, there is illustrated a disposable garment 50 incorporating an elastic laminate made according to the present invention. Although training pants are shown in FIG. 4, it will be understood that use of the elastic laminate produced according to the present invention is not limited to such articles and may also be used in a wide variety of applications including, but not limited to, diapers, incontinence devices, industrial work wear, surgical drapes and gowns and the like. Referring again to FIG. 4, the disposable garment 50 includes waste containment section 52 and two side panels 54 and 16 defining a waist opening 58 and a pair of legs openings 60 and 62. FIG. 4 illustrates the disposable garment 50 fitted on a wearer's torso 64 in dashed lines. Side panel 54 includes stretchable side member 66 and stretchable side member 68 connecting intermediate member 70 which is made of a non-stretchable material. Similarly, side panel 56 includes stretchable side member 72 and stretchable side member 74 connecting intermediate member 76 which is made of a non-stretchable material. Disposable garment 50 also includes front waist elastic member 78 and rear waist elastic member 80 for providing additional elasticity along waist opening 58. Leg elastics 82 are provided with waist containment section 52 between side panels 54 and 56.

The elastic laminate of the present invention may be used to form various portions of the disposable garment 50 and particularly, the side panels 54 and 56. The elastic laminate may also be used in the leg elastics 82 of the disposable garment 50.

The resulting elastic laminate has significantly improved elastic properties at body temperature. The resulting elastic material suffers no loss of elasticity and retains its dimensional stability over time under actual use conditions.

Of course, it should be understood that a wide range of changes and modifications can be made to the embodiments described above. It is, therefore, intended that the foregoing description illustrate rather than limit this invention and that it is the following claims, including all equivalents, that define this invention.

What is claimed is:

1. A disposable garment comprising a laminate composition having improved elastic properties comprising a dimensionally stable polymeric material, wherein said polymeric material comprises a blend of a styrene block copolymer and polyphenylene ether.

2. The disposable garment of claim 1 wherein the ratio of the styrene in the block copolymer to the polyphenylene ether is from about 1:1.5 to about 2:1.

3. The disposable garment of claim 2 wherein the ratio of the styrene in the block copolymer to the polyphenylene ether is about 1:1.

4. The disposable garment of claim 1 wherein said laminate composition has a percent load loss no greater than about 25%.

5. The disposable garment of claim 1 wherein said garment is a diaper.

6. The disposable garment of claim 1 wherein said garment is a training pant.

7. The disposable garment of claim 1 wherein said garment is an adult incontinence garment.

8. The disposable garment of claim 1 wherein said garment is a protective garment.

9. The disposable garment of claim 1 wherein said garment is a personal care absorbent product selected from the group consisting of diapers, training pants and adult incontinence garments.

10. The disposable garment of claim 9 wherein the styrene block copolymers are selected from the group consisting of triblock copolymers having the general formula A-B-A' where A and A' are each rigid blocks of polystyrene and tetrablock copolymers having the formula A-B-A-B where A is a styrene block.

11. The disposable garment of claim 9 wherein the ratio of the styrene in the block copolymer to said polyphenylene ether is from about 1:1.5 to about 2:1.

12. The disposable garment of claim 10 wherein the ratio of the styrene in the block copolymer to said polyphenylene ether is about 1:1.

13. The disposable garment of claim 10 wherein said styrene block copolymers further comprise, tackifier and polyethylene wax.

* * * * *